(12) United States Patent
Matheny

(10) Patent No.: US 9,532,943 B2
(45) Date of Patent: *Jan. 3, 2017

(54) DRUG ELUTING PATCH FOR THE TREATMENT OF LOCALIZED TISSUE DISEASE OR DEFECT

(75) Inventor: Robert Matheny, Norcross, GA (US)

(73) Assignee: CORMATRIX CARDIOVASCULAR, INC., Roswell, GA (US)

( * ) Notice: Subject to any disclaimer, the term of this patent is extended or adjusted under 35 U.S.C. 154(b) by 142 days.

This patent is subject to a terminal disclaimer.

(21) Appl. No.: 13/328,287

(22) Filed: Dec. 16, 2011

(65) Prior Publication Data

US 2012/0156255 A1   Jun. 21, 2012

Related U.S. Application Data

(60) Provisional application No. 61/425,172, filed on Dec. 20, 2010.

(51) Int. Cl.
*A61K 31/40* (2006.01)
*A61K 9/00* (2006.01)

(52) U.S. Cl.
CPC .................. *A61K 9/0024* (2013.01)

(58) Field of Classification Search
CPC .................................. A61K 9/0024
USPC .................. 424/400; 514/275, 277, 311
See application file for complete search history.

(56) References Cited

U.S. PATENT DOCUMENTS

| | | | |
|---|---|---|---|
| 4,902,508 A | 2/1990 | Badylak | |
| 6,056,970 A * | 5/2000 | Greenawalt et al. | 424/426 |
| 6,096,347 A | 8/2000 | Geddes | |
| 6,579,538 B1 | 6/2003 | Spievack | |
| 7,785,615 B2 | 8/2010 | Dave | |
| 2003/0009145 A1 | 1/2003 | Struijker-Boudier | |
| 2004/0191226 A1 | 9/2004 | Badylak | |
| 2005/0249771 A1 * | 11/2005 | Malaviya et al. | 424/423 |
| 2006/0002979 A1 * | 1/2006 | Ashammakhi et al. | 424/426 |
| 2006/0178424 A1 | 8/2006 | Nattel | |
| 2006/0251702 A1 | 11/2006 | Janis | |
| 2007/0014773 A1 * | 1/2007 | Matheny et al. | 424/93.21 |
| 2007/0014868 A1 | 1/2007 | Matheny | |
| 2007/0014869 A1 | 1/2007 | Matheny | |
| 2007/0014870 A1 | 1/2007 | Matheny | |
| 2007/0014871 A1 | 1/2007 | Matheny | |
| 2007/0014872 A1 | 1/2007 | Matheny | |
| 2007/0014873 A1 | 1/2007 | Matheny | |
| 2007/0014874 A1 | 1/2007 | Matheny | |
| 2007/0219487 A1 | 9/2007 | Mazgalev | |
| 2008/0167727 A1 | 7/2008 | Cook | |
| 2008/0167728 A1 | 7/2008 | Cook | |
| 2008/0171092 A1 | 7/2008 | Cook | |
| 2008/0274184 A1 | 11/2008 | Hunt | |
| 2009/0142409 A1 | 6/2009 | Firestone | |
| 2010/0233235 A1 | 9/2010 | Lewis | |
| 2011/0104230 A1 | 5/2011 | Ardawi | |

FOREIGN PATENT DOCUMENTS

| | | |
|---|---|---|
| AU | 20100215095 | 8/2010 |
| BR | PI1008628-5 | 8/2010 |
| CA | 2752899 | 8/2010 |
| CN | 2010800170125 | 8/2010 |
| EP | 10744236.0 | 8/2010 |
| HK | 12106312.4 | 8/2010 |
| IL | 214706 | 8/2010 |
| IN | 6496/DELNP/2011 | 8/2010 |
| JP | 2011-551181 | 8/2010 |
| KR | 10-2011-7021655 | 8/2010 |
| MX | a/2011/008735 | 8/2010 |
| NZ | 595188 | 8/2010 |
| WO | WO2005/097219 | 3/2005 |
| WO | WO2007/011644 | 1/2007 |
| WO | WO2010/096458 | 8/2010 |

OTHER PUBLICATIONS

Aranaz et al.; Title: Functional characterization of chitin and chitosan; Current Chemical Biology, 2009, vol. 3 (2), pp. 203-230; published by Bentham Science Publisher Ltd.*
International Preliminary Report on Patentability issued Aug. 23, 2011 by the International Bureau for PCT/US2010/024441 Filed Feb. 17, 2010 (Applicant—CorMatrix Cardiovascular, Inc. // 1st Named Inventor—Matheny) (8 pages).
Claims amendment filed Apr. 3, 2012 with the European Patent Office for application EP 2398502 filed Feb. 17, 2010 (Applicant—CorMatrix Cardiovascular, Inc. // 1st Named Inventor—Matheny) (8 pages).
Badylak S, et al. Extracellular matrix for myocardial repair, Heart Surg Forum 6, E20-26 (2003).
Berthonneche C, et al. New insights into the pathological role of TNF-a in early cardiac dysfunction and subsequent heart failure after infarction in rats, Am J Physiol (Heart Circ Physiol) 287, H340-H350 (2004).
Blanchard, L, et al. Non-antiarrhythmic agents for prevention of postoperative atrial fibrillation: role of statins. Current Opinion in Anesthesiology 20, 53-56 (2007).

(Continued)

*Primary Examiner* — Yanzhi Zhang
(74) *Attorney, Agent, or Firm* — Francis Law Group

(57) ABSTRACT

A polymeric matrix for delivery of an HMG CoA reductase inhibitor such as a statin to tissue such as cardiac tissue in need thereof for the treatment or prevention of a disease or defect such as atrial fibrillation has been developed. In the preferred embodiment, a statin is delivered by means of a patch sutured to cardiac tissue at the time of cardiothoracic surgery. In the most preferred embodiment, the patch is a biodegradable material providing controlled or sustained release over a prolonged period of time, such as a week. Suitable materials include extracellular matrix, or other biodegradable hydrogels or polymeric materials providing sustained or controlled release of statin at the site of application.

14 Claims, 2 Drawing Sheets

(56) References Cited

OTHER PUBLICATIONS

Boos CJ, et al. Is atrial fibrillation an inflammatory disorder? Eur Heart J 27, 136-149 (2006).

Christman KL, et al. Fibrin glue alone and skeletal myoblasts in a fibrin scaffold preserve cardiac function after myocardial infarction, Tissue Eng 10, 403-409 (2004).

Collard, et al. Preoperative statin therapy is associated with reduced cardiac mortality after coronary artery bypass graft surgery, J thorac Cardiovasc Surg 132, 392-400 (2006).

Davis ME, et al. Injectable self-assembling peptide nanofibers create intramyocardial microenvironments for endothelial cells, Circulation 111, 442-450 (2005).

Echahidi N, et al. Mechanisms, prevention, and treatment of atrial fibrillation after cardiac surgery, J Am Coll Cardiol 51, 793-801 (2008).

Ji Q, et al. Effect of preoperative atorvastatin therapy on atrial fibrillation following off-pump coronary artery bypass grafting, Circ J 73, 2244-2249 (2009).

Koniari I, et al. Pharmacologic prophylaxis for atrial fibrillation following cardiac surgery: a systematic review, J Cardiothoracic Surg 5, 121-130 (2010).

Landa N, et al. Effect of injectable alginate implant on cardiac remodeling and function after recent and old infarcts in rat, Circulation 117, 1338-1396 (2008).

Liakopoulos OJ, et al. Impact of preoperative statin therapy on adverse postoperative outcome in patients undergoing cardiac surgery: a meta-analysis of over 30,000 patients, Eur Heart J 29, 1548-1559 (2008).

Lindsey ML, et al. Extracellular Matrix remodeling following myocardial injury, Ann Med 35, 316-326 (2003).

Mitchell AJ, et al. Comparison of initial cell retention and clearance kinetics after subendocardial or subepicardial injections of endothelial progenitor cells in a canine myocardial infarction model, J Nucl Med 51, 413-417 (2010).

Naji F, et al. Comparison of atorvastatin and simvastatin in prevention of atrial fibrillation after successful cardioversion, Int Heart J 50, 153-160 (2009).

Patti G, et al. Randomized trial of atorvastatin for reduction of postoperative atrial fibrillation in patients undergoing cardiac surgery. Results of ARMYDA-3 (Atorvastatin for Reduction of Myocardial Dysrhythmia After cardiac surgery) study, Circulation 114, 1455-1461 (2006).

Robinson KA, et al. Extracellular matrix scaffold for cardiac repair, Circulation 112, I135-143 (2005).

Schnabel, R, et al. Relation of multiple inflammatory biomarkers to incident atrial fibrillation. Am J Cariol 104(1), 92-96 (2009).

Thielmann, et al. Lipid-lowering effect of preoperative statin therapy on postoperative major adverse cardiac events after coronary artery bypass surgery, J Thorac Cariovasc Surg 134, 1143-1149 (2007).

Wang C-Y, et al. Pleiotropic effects of statin therapy, Trends Mol Med 14, 37-44 (2008).

Zhao, et al. Improvement in cardiac function with small intestine extracellular matrix is associated with recruitment of C-Kit cells, myofibroblasts, and macrophages after myocardial infarction, J Am Coll Cardiol 55, 1250-1261 (2010).

\* cited by examiner

DRUG ELUTING PATCH FOR THE TREATMENT OF LOCALIZED TISSUE DISEASE OR DEFECT

CROSS REFERENCE TO RELATED APPLICATIONS

This application claims the benefit of and priority to U.S. Provisional Application No. 61/425,172 filed Dec. 20, 2010, which is incorporated herein by reference in its entirety.

JOINT RESEARCH AGREEMENT NOTICE

This application and all inventions embodied therein are subject to the terms of a Joint Research Agreement by and between Saint Joseph's Translational Research Institute, Inc. and CorMatrix Cardiovascular, Inc.

FIELD OF THE INVENTION

The present invention is generally in the field of drug delivery to a heart, particularly for treatment of atrial fibrillation.

BACKGROUND OF THE INVENTION

An arrhythmia is a disorder with the speed or rhythm of the heartbeat. Atrial fibrillation (AF) is the most common type of arrhythmia. The cause is a disorder in the heart's electrical system. Atrial fibrillation (AF) is a significant complication that occurs in about 30% of the patients undergoing cardiac surgery. The risk of AF increases with age. Patients over 30 years of age exhibit a 75% increase in AF for every decade of life. The molecular mechanism of acute AF following cardiac surgery is not well understood. Impaired hemodynamics, endothelial dysfunction, inflammation, oxidative stress, and thrombosis have been implicated as important contributors to AF. In AF patients, turbulent blood flow impacts nitric oxide (NO) bioavailability, producing vascular dysfunctions and activation of coagulation system which may contribute to the high rate of embolic events. Drugs that reduce vascular inflammation and improve vascular dysfunction and NO bioavailability may be efficacious for the prevention and treatment AF. One such class of drugs that exhibit these vascular and cardiac pleotropic effects are the HMG-COA inhibitors statins. It is widely documented that statins reduce vascular inflammation, oxidative stress and improve NO generation. Statins also modulate small GTPase including Rac1 by isoprenylation. Rac1 binds to p67phox and leads to activation of the NADPH oxidase system and subsequent generation of reactive oxygen species (ROS). Indeed, Rac1 activity is closely related to ROS production and ROS generated by NADPH oxidase in response to growth factors and inflammatory cytokines is mediated by Rac1. Importantly, statins inhibit Rac1-mediated NADPH oxidase activity and thereby reduce angiotensin II-induced ROS production and hypertrophy in smooth muscle and heart. Rac 1 has been shown to play role in the pathogenesis of AF. Transgenic mice overexpressing Rac1 exhibit conduction abnormalities and atrial fibrosis.

Observational and prospective studies have suggested beneficial effect of statin on AF (Liakopoulos O J et al. Euro. Heart J. 29; 1548-4559 (2008)) However, results of other prospective studies have been negative. For example, Collard, et al. (J. Thorac. Cardiovasc. Surg. 2006, 132:392) and Thielman, et al. (J. Thorac. Cardiovas. Surg. 2007; 134, 1143) failed to show decrease in all cause mortality in patients using statin before cardiac surgery.

There have been a limited number of trials on the effect of systemically administered statin on atrial fibrillation. The results are inconsistent and, in most cases, not statistically significant. For example, Negi, et al., J. Cardiovasc. Electrophysiol. April; 22(4):414-9 (2011) reported on a randomized, double-blinded, placebo-controlled trial, where patients with atrial fibrillation/flutter (AF) were randomized to receive either atorvastatin 80 mg (n=33) or placebo (n=31) before CV. Treatment was continued for 12 months or until AF recurred. They concluded that high-dose atorvastatin did not reduce the recurrence of AF after CV. It reduced selective markers of inflammation without affecting systemic oxidative stress. Failure of atorvastatin to prevent AF recurrence may be due to its failure to affect oxidative stress. Another study has shown that atorvastatin but not simvastatin was effective in prevention of AF (Naji et al Int. Heart J. 50, 153-160 (2009)). The inconsistent effect of statins could also be due to inadequate and inconsistent concentration at the target site when administered orally. Further limitations to the efficacy may be due to variability of patient's response to liver metabolism when delivered orally. The high dose of statins also increase the risk of liver and muscle toxicities. Alves, et al. Arg. Bras Cardiol. 2010 Sep. 24. pii: S0066-782X2010005000129. [Epub ahead of print] reported on a study to evaluate whether the chronic and regular use of statins, for a period of six months, prevents atrial fibrillation after elective cardiac surgery. In the postoperative period, atrial fibrillation was present in 42 patients (39%) of the sample, including 11 (26%) people that had used statins on a regular basis in the preoperative period and 31 (74%) who had not. They concluded that the regular use of statin, for six months or more in the preoperative period, reduced the incidence of atrial fibrillation after elective cardiac surgery. In a third report, Kinoshita, et al., Circ. J. 74(9):1846-51 (2010). Epub 2010 Jul. 6, reported on a study to assess the preventive effect of preoperative statin treatment on atrial fibrillation (AF) after elective isolated off-pump coronary artery bypass grafting (off-pump CABG) in propensity score-matched Japanese patients. 584 patients were retrospectively reviewed from among 770 consecutive patients undergoing isolated CABG by the same surgeon (99.2% with off-pump technique without conversion to cardiopulmonary bypass) between 2002 and 2009, after excluding emergency (n=150), chronic AF (n=30), and use of cardiopulmonary bypass (n=6). 364 patients received statin at least 5 days before operation and 220 patients received no statin. The concluded that preoperative statin significantly reduces the incidence of AF after elective isolated off-pump CABG in Japanese patients.

It is therefore an object of the present invention to provide a means for treating or preventing atrial fibrillation.

SUMMARY OF THE INVENTION

A polymeric matrix for delivery of an HMG CoA reductase inhibitor such as a statin to tissue such as cardiac tissue in need thereof for the treatment or prevention of a disease or defect such as atrial fibrillation has been developed. In the preferred embodiment, a statin is delivered by means of a patch sutured to cardiac tissue at the time of cardiothoracic surgery. In the most preferred embodiment, the patch is a biodegradable material providing controlled or sustained release over a prolonged period of time, such as a week. Suitable materials include extracellular matrix, or other

DETAILED DESCRIPTION OF THE INVENTION

I. Compositions

A. HMG CoA Reductase Inhibitors

Figure 1:
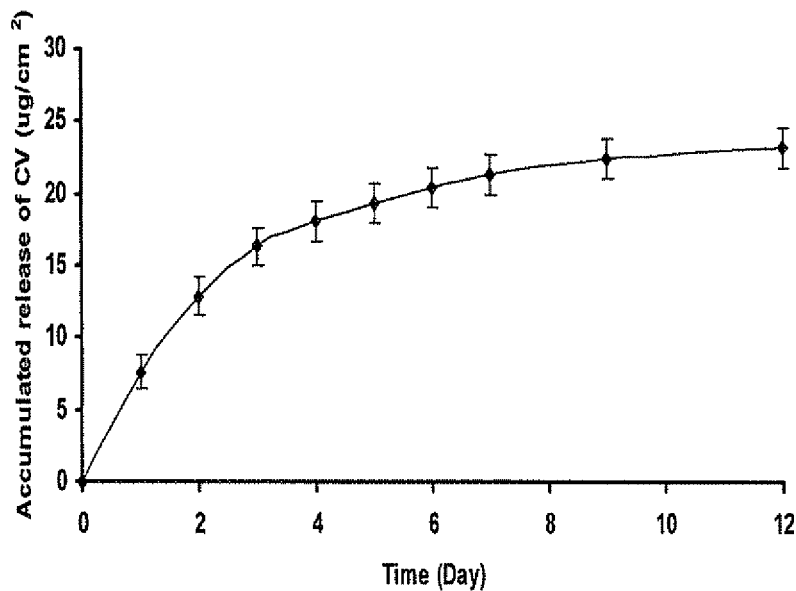
FIG. 1 is a graph of cumulative release of cerivastatin from an ECM patch over time in days.

Statins or HMG-CoA reductase inhibitors are a class of drug used to lower cholesterol levels by inhibiting the enzyme HMG-CoA reductase, which plays a central role in the production of cholesterol in the liver. Increased cholesterol levels have been associated with cardiovascular diseases (CVD), and statins are therefore used in the prevention of these diseases. The best known of the statins is atorvastatin, marketed as LIPITOR® and manufactured by Pfizer. As of 2010, a number of statins are on the market: atorvastatin (LIPITOR® and TORVAST®), fluvastatin (LESCOL®), lovastatin (MEVACOR®, ALTOCOR®, ALTOPREV®), pitavastatin (LIVALO®, PITAVA®), pravastatin (PRAVACHOL®, SELEKTINE®, LIPOSTAT®), rosuvastatin (CRESTOR®) and simvastatin (ZOCOR®, LIPEX®). Several combination preparations of a statin and another agent, such as ezetimibe/simvastatin, sold as VYTORIN®, are also available.

The most preferred statin is cerivastatin, (3R,5S,6E)-7-[4-(4-fluorophenyl)-5-(methoxymethyl)-2,6-bis(propan-2-yl)pyridin-3-yl]-3,5-dihydroxyhept-6-enoic acid.

Systemic dosages for statins are generally between 10-80 mg daily, with lower dosages for local delivery in a matrix being effective for treatment of a disorder such as atrial fibrillation. Various doses of cerivastatin, as desired for efficacy could be incorporated into a patch and then released over time. For example, a patch can be incubated with 10 mg to achieve high concentration at the local site or 10 μg cerivastatin to achieve low concentration or any concentrations in between. The duration of application or statin release can be from one day to 30 days for prevention or treatment of AF.

B. Matrices for Administration of HMG CoA Reductase Inhibitor

In a preferred embodiment, the inhibitors are administered from FDA approved cardiac patches formed from extracellular matrix material ("ECM") that are used for pericardial reconstruction and prevention of adhesion. These patches are used to locally deliver drugs following cardiac surgery. Pharmacologically levels of statin can be incorporated in an ECM patch and then released over time in vivo. Implantable acellular xenograft derived from the extracellular matrix (ECM) is used for pericardial repair and cardiac reconstruction (Badylak et al., 2003; Badylak et al., 2006; Gerdisch et al., 2009; and Robinson et al., 2005b and has been proven safe and FDA approved for use in humans (Badylak, et al., Acta Biomater, vol. 5(1), pp. 1-13(2009); the noted references being incorporated by reference herein).

Other natural materials may be used for drug delivery. For example, Miyagi, et al., Biomaterials 2010 Oct. 28, reported on the use of a biodegradable collagen patch for delivery of VEGF for myocardial repair. Alginate scaffolds are described by Shachar, et al., in Acta Biomater. 7(1):152-62 (2011). Decellularized matrices are described by Singelyn, et al. in J Cardiovasc Transl Res. 3(5):478-86 (2010). Polymeric woven or non-woven matrices can be utilized. For example, non-biodegradable polyurethane matrices having seeded therein myoblasts is reported by Giraud, et al., in Artif Organs. 34(6):E184-92 (2010). Ito, et al., reported on the use of a polytetrafluorethylene (PTEF) patch in Ann Thorac Surg. 89(5):1620-4 (2010). Fibrinogen matrices or TachoSil, a sponge impregnated with human fibrinogen and thrombin, can be used for short term delivery, although the delivery time is preferably longer than the two to three days obtainable at most with a fibrin matrix.

Preferably the polymeric materials are biodegradable. Representative examples include the polyhydroxy acids poly(lactic acid), poly(glycolic acid) and copolymers thereof, and polyhydroxyalkanoates such as poly(4-hydroxybutyrate), all of which are FDA approved for use in humans. Poly(4-hydroxybutyrate) is available from Tepha Inc of Mass. and has been used in studies of heart valve leaflets made from woven meshes. A bilayered patch made of a poly[ethylene glycol]-based matrix and poly[lactide-co-caprolactone] backing layer loaded with amiodarone (10 mg per patch) is reported by Bolderman in J Thorac Cardiovasc Surg. 140(4):904-10 (2010). Chen, et al., describes an elastomeric patch derived from poly(glycerol sebacate) for delivery of cardiomyocytes differentiated from embryonic stem cells to the heart in Biomaterials. 31(14):3885 (2010).

C. Other Bioactive Agents

Other bioactive materials can also be delivered with this technology. For example, vascular epithelial growth factor, as reported by Miyagi, et al. (2010). Other materials may be cellular, preferably autologous, such as stem cells, myoblasts or B cells. Stein, et al., reported on the reduction of fibrosis-related arrhythmias by chronic renin-angiotensin-aldosterone system inhibitors in *Am J Physiol Heart Circ Physiol.* 299(2):H310-21 (2010). The authors tested eplerenone; losartan; and cotreatment with eplerenone and losartan. Myocardial fibrosis increases arrhythmia vulnerability of the diseased heart. Bolderman (2010) describes administration of amiodarone.

Preferred actives to include with matrix include antiinflammatory corticosteroids, antioxidants such as liopcyanin, SiRNA for Rac1, anti-thrombotic and antiplatelet drugs such as Plavix.

II. Methods of Administration

A. Disorders to be Treated

Postoperative atrial fibrillation is the most common arrhythmic complication following cardiac surgery with a reported incidence between 31.9% and 63.6% in patients undergoing various cardiac procedures [Auer et al., 2005; Creswell et al., 1993; Echahidi et al., 2008]. Patients with postoperative AF are at significantly increased risk of hypotension, congestive heart failure, thrombo-embolic events such as a cerebrovascular accident and the need for postoperative implantation of a permanent pacemaker or implantable defibrillator. Complications of postoperative AF has been associated with an increased length of stay (LOS)

in the ICU or postoperative telemetry floor. A recent study from the Commonwealth of Virginia found that the average additive cost of isolated postoperative AF following isolated CABG was $2,574 per patient [Speir et al., 2009]. Annual costs to the U.S. healthcare system due to postoperative AF and its sequelae are estimated to run in excess of $2 billion [Echahidi et al., 2008]. Further, chronic AF affects more than 3 million people in US and about 5 million in western Europe The etiology of underlying pathogenesis of chronic AF is similar which includes, inflammation, oxidative stress and fibrosis. With increase in aging population, the estimated number of cases of AF in the USA are expected to reach 15 million by 2050.

An optimum therapy for postoperative AF is yet to be available. Current interventions include beta-adrenergic blockers, perioperative amiodarone, sotalol, nondihydropyridine calcium channel blockers, magnesium sulfate and biatrial pacing F. The efficacy of these treatments is variable and accompanied with risk.

In a preferred embodiment, a composition of the invention is applied to an area having ischemic damage or atrial fibrillation. Statins should reduce the incidence of postoperative AF. The beneficial effect of statins on the pathophysiology of AF is supported by several observational and prospective studies, suggesting that statin treatment is beneficial to patients undergoing electrical cardioversion, postoperative AF, paroxymal AF, and AF associated with coronary artery disease and left ventricular dysfunction. A small prospective, randomized, placebo controlled, double blind ARMYDA-3, Atorvastatin for Reduction of Myocardial Dysrhythmia after cardiac surgery, study has shown that treatment with 40 mg/day atorvastatin produced 61% reduction in risk of postoperative AF. Another recent study by Qiang et al, Circ J, vol. 73, pp. 2244-2249 (2009), showed that atorvastatin 20 mg/day, initiated 1 week before elective off-pump CABG and continued in the postoperative period, significantly decreases postoperative AF.

At present, suitable pharmacological agents for the prevention of postoperative AF are not available. Several prospective studies strongly suggest that statin class of drugs reduced post-operative AF. A high dose of statin and preoperative dosing appears to be required for an optimum efficacy. Since high doses of statins are required to achieve improvement of vascular functions, the therapeutic doses of statins either do not achieve direct benefit on vascular functions or achieve only partial benefit. Further limitations to efficacy may be due to patient variability and variable drug levels at the local site. High doses of statins required to achieve blood levels that produce direct beneficial effects on vascular functions increase risk of liver and muscle toxicities.

Therefore, local delivery of statins following cardiac surgery achieves greater efficacy on vascular and cardiac functions, while avoiding the increased risk of liver and muscle toxicity. Since AF is a regional pathogenesis, and consistent levels of drug are required for optimum therapy, local delivery of statin produces maximum efficacy and minimum adverse effects.

B. Methods of Administration

In a preferred embodiment, a drug is mixed with the material forming the matrix and the formed matrix is administered thereafter. This is a preferred method for materials, such as extracellular matrix material matrices and polymeric meshes, which are sutured to a tissue to be treated at the time of implantation, typically during surgery. Alternatively, for example, in the case of a fibrinogen matrix, a drug is mixed with the fibrinogen and thrombin added, and the polymerizing mixture applied to heart tissue.

The actual dose of a statin, preferably cerivastatin, as desired for efficacy, to be incorporated into a patch for release over time can be determined by extrapolation from in vitro and animal studies. For example, a patch can be loaded with 10 mg/cm2 to achieve high concentrations at a local site in a heart or vasculature or as low as 10 $\mu g/cm_2$ cerivatatin to achieve low concentrations or any concentrations in between. The duration of treatment or statin release can vary from 1 day to 30 days for the prevention of AF.

The present invention will be further understood by reference to the following non-limiting inventions.

Example 1

In Vitro Efficacy of ECM Patch Loaded with Cerivastatin

A tissue engineered ECM patch with desired cerivastatin release kinetics was prepared. Preliminary studies have demonstrated that cerivastatin can be incorporated in the ECM patch. Studies of loading conditions and release kinetics have shown that cerivastatin release kinetics can be successfully optimized to achieve drug levels that produce antiinflammatory effects. Studies were then conducted to determine optimal conditions to produce uniformly drug loaded patches for in vivo studies.

Materials and Methods

Tissue Engineered Pericardial Repair Patch Preparation:
Determination of the Kinetics of Cerivastatin Release from the ECM Patch:

Loading of cerivastatin in the patch was performed by incubation in different concentrations of cerivastain in phosphate buffered saline (PBS) at 25° C. for 24 hours. The patch was then washed with fresh PBS three times. The kinetics of cerivastatin release was then determined by incubation in 0.5 ml of PBS at 25° C. The supernatants were collected and replenished with fresh PBS at 4 hours, 1, 2, 3, 4, 5, 6, 7, 10, 15 days. The quantity of cerivastatin in the supernatants was determined using HPLC. All experiments were performed in triplicate.

Determination of the Cerivastatin by HPLC:

Cerivastatin was measured by separating on a C18 ultra aqueous analytical column (250 mm×4.6 mm, 5 µm) from RESTEK. Mobile phase was mixture of 90% acetonitrile and 10% water with flow rate at 1 mL/min. Cerivastatin was detected spectrophotometrically at 220 nm.

Determination of Anti-Inflammatory Activity of Cerivastatin Released from the Patch:

THP-1 cells were seeded at $6 \times 10^5$ cells/ml into 12-well transwell plates. Cells were pre-treated with cerivastatin, patch alone or cerivastatin loaded patches for 1 h and then treated with 200 ng/mL LPS for 24 h. The supernatants were collected for ELISA. Cells were used for RNA extraction and quantitative PCR.

Measurement of MCP-1 in the Cell Supernatants:

A commercial enzyme linked-immuno-sorbent assay (ELISA) kits (R&D systems) was used to quantify MCP-1 levels in the cell free supernatants, according to the manufacturer's protocols. The absorbance at 450 nm and 570 nm (reference wavelength) were read using a microplate reader (Synergy 2, Biotek). All experiments were performed in triplicate.

Real-Time Reverse Transcription-PCR Analysis:

Total RNA was extracted using the RNeasy Kit (Qiagen, Valencia, Calif.) according to the manufacturer's instructions. After reverse transcription (RT) using the RNA PCR kit (AMV) version 2.1, PCR was performed using an ABI Prism 7500 Sequence Detection System (Applied Biosystems, Foster City, Calif.) and QuantiTect SYBR Green PCR Master Mix (Qiagen, Valencia, Calif.). All reactions were carried out in triplicate, and the mRNA copy numbers of specific genes among the total RNA extracts were calculated. All data were expressed as the mean+/−standard deviation of the triplicate wells.

Results

Different amounts of cerivastatin can be loaded into the ECM patch to achieve the desired level of release for efficacy. When the patch was incubated with 100 μg/ml cerivastatin, the drug release was 15-20 μg for the first 4 days and then slowly released over the next 10 days.

Figure 2:
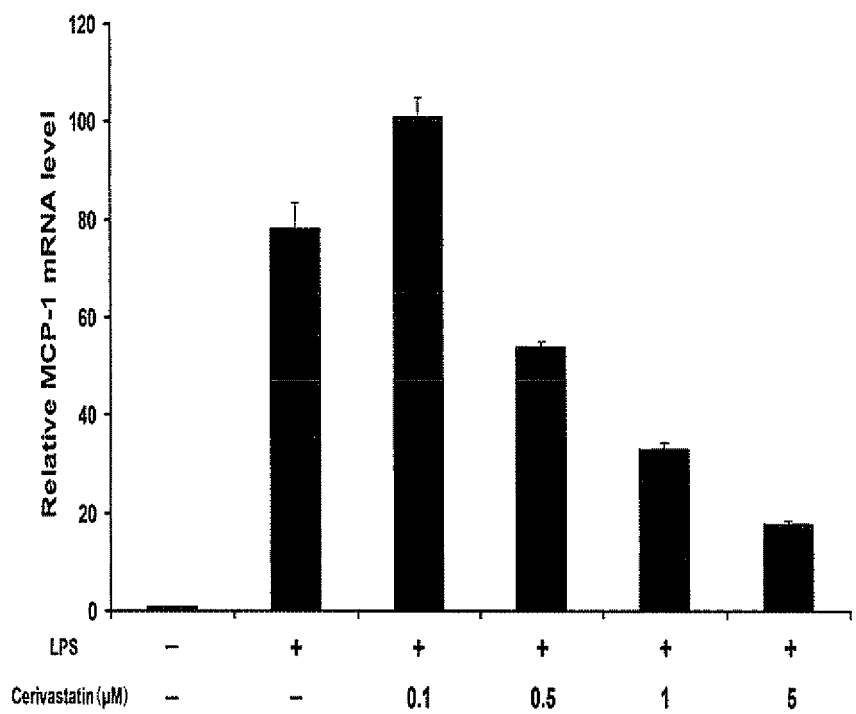
FIG. 2 is a graph of relative MCP-1 mRNA levels as a function of the amount of cerivastatin (μM) in vitro.

As shown in FIG. 2, this level of cerivastatin was adequate to achieve complete inhibition of inflammatory chemokine MCP-1 generation by human monocyte cells THP-1. Much greater levels of cerivastatin (800-900 μg/cm2) can be loaded into the patch when incubated at a higher concentration (2 mg/ml). Levels of loading and release are dependent on the statin that is used.

Figure 3:
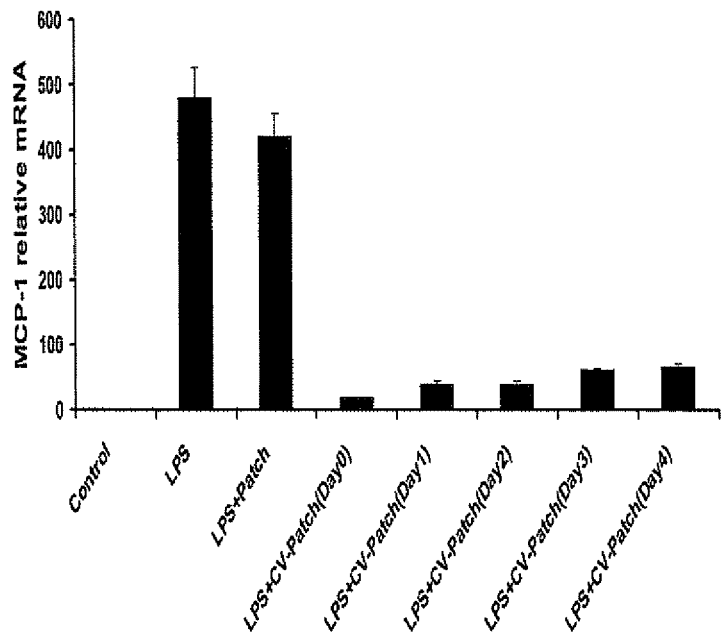
FIG. 3 is a graph of MCP-1 relative mRNA as a function of LPS, LPS+patch, LPS+cerivastatin+patch on day 1, LPS+cerivastatin+patch on day 2, LPS+cerivastatin+patch on day 3, and LPS+cerivastatin+patch on day 4 in vitro.

FIG. 3 shows that when the patch was loaded by incubation with 100 μg/ml cerivastatin and then placed on the upper chamber of a transwell plate in which inflammatory cells were placed in lower chamber such that the patch and the cells were separated by the culture medium, the cerivastatin released from the patch diffused to the cells and blocked the generation of proinflammatory chemokine MCP-1. These conditions are representative of in vivo conditions. The amount of cerivastatin released from the patch was sufficient to produce this effect for more than 4 days. These data show that cerivastatin amounts would be sufficient for blocking inflammation mediator during AF which mostly occurs during the 2-4 days post cardiac surgery.

Figure 4:
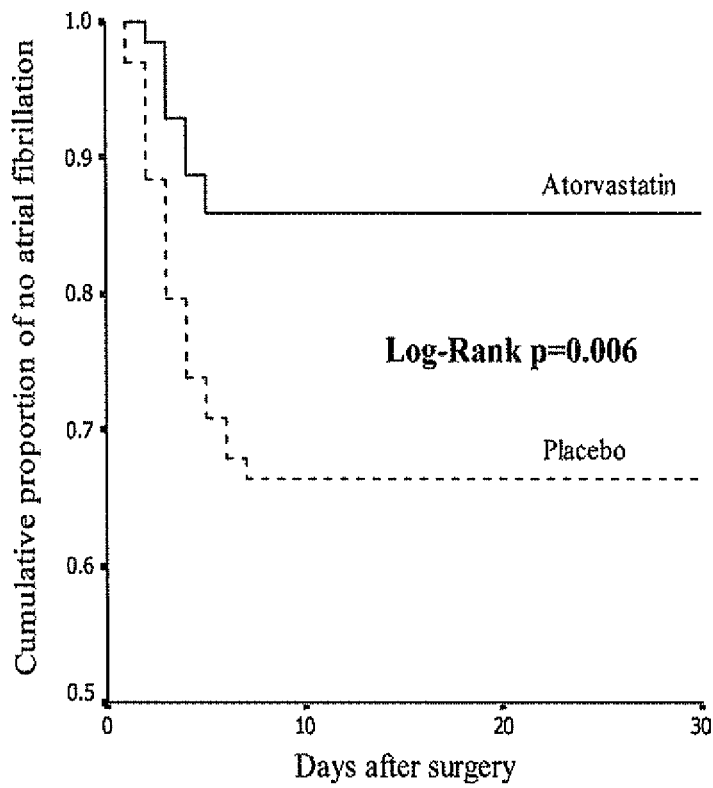
FIG. 4 is graph of the cumulative proportion of no atrial fibrillation as a function of days after surgery, comparing placebo and atrovastatin.

Cerivastatin also blocked expression of the inflammatory receptor CCR2. This activity of cerivastain was different from other statins and thus may produce a greater impact in decreasing inflammation after surgery FIG. 4 shows that patients pretreated with atorvastatin orally had a reduced incidence of AF. The data suggests that local delivery of a low dose of a statin, at a dose expected to produce efficacy in treatment of AF, would not have the risk associated with a systemically delivered statin. Furthermore, local delivery using a patch can achieve desired and consistent level in target tissue.

Example 2

Determination of In Vivo Efficacy of a Cerivastatin Eluting Tissue Engineered Patch in a Dog Model of AF The release kinetics demonstrated in Example 1 is suitable to produce tissue levels of cerivastatin to produce biological efficacy of cerivastatin for about a week. Since the majority of AF occurs 2-3 days post coronary artery bypass graft ("CABG"), a patch should provide ideal local drug treatment. A dog model of pericardites has been previously used for testing efficacy of systemically delivered statin. See, for example, Nattell, et al. Prog Biophys Mol Biol., vol. 98(2-3), pp. 328-39 (2008); Okumura, et al., J Am Coll Cardiol., vol. 17(2), pp. 509-18 (1991); and Pageet, et al., J Am Coll Cardiol., vol. 8(4) UT, pp. 872-9 (1986).

We claim:

1. A patch for treating a cardiac disorder, comprising:
a matrix comprising acellular extracellular matrix (ECM); and
a HMG CoA reductase inhibitor comprising cerivastatin, said cerivastatin comprising in the range of 10 μg/cm$^2$-10 mg/cm$^2$ of said ECM matrix,
said ECM matrix being capable of modulating inflammation of post-operative cardiac tissue when administered thereto, said inflammation modulation comprising inhibiting localized expression of monocyte chemoattractant protein 1 (MCP-1) and C-C chemokine receptor type 2 (CCR2).

2. The patch of claim 1, wherein said HMG CoA reductase inhibitor is dispersed within said ECM matrix.

3. The patch of claim 1, wherein said ECM matrix is in the form of a graft.

4. The patch of claim 1, wherein said ECM matrix is configured to be applied as a spray.

5. The patch of claim 1, wherein said ECM matrix is configured to be applied as a biological glue.

6. The patch of claim 1, wherein said ECM matrix further includes a pharmacological agent component comprising an anti-thrombotic agent.

7. The patch of claim 1, wherein said ECM matrix is in the form of a hydrogel.

8. The patch of claim 1, wherein said ECM matrix is in the form of a woven matrix.

9. The patch of claim 1, wherein said ECM matrix is in the form of a non-woven matrix.

10. A method for treating tissue injury or defect comprising administering to or near the patch the device of claim 1.

11. The method of claim 10 wherein the tissue injury or defect is caused by ischemia.

12. The method of claim 10 wherein the tissue is cardiac tissue and the defect is atrial fibrillation.

13. The method of claim 10 wherein the patch is administered during surgery.

14. The method of claim 10 wherein the patch is administered through a catheter or as part of a stent.

* * * * *